United States Patent
Cha et al.

(10) Patent No.: US 10,597,344 B2
(45) Date of Patent: Mar. 24, 2020

(54) METHOD FOR PREPARING 1,3-CYCLOHEXANEDIMETHANOL

(71) Applicant: LOTTE CHEMICAL CORPORATION, Seoul (KR)

(72) Inventors: Mi Sun Cha, Daejeon (KR); Seong Hwan Choi, Daejeon (KR); Sung Min Kim, Daejeon (KR); Sung Joon Park, Daejeon (KR); Chan Yeong Yun, Daejeon (KR); Young Heon Choi, Daejeon (KR)

(73) Assignee: Lotte Chemical Corporation, Seoul (KR)

( * ) Notice: Subject to any disclaimer, the term of this patent is extended or adjusted under 35 U.S.C. 154(b) by 0 days.

(21) Appl. No.: 16/331,506

(22) PCT Filed: Sep. 5, 2017

(86) PCT No.: PCT/KR2017/009715
§ 371 (c)(1),
(2) Date: Mar. 7, 2019

(87) PCT Pub. No.: WO2018/048175
PCT Pub. Date: Mar. 15, 2018

(65) Prior Publication Data
US 2019/0202761 A1    Jul. 4, 2019

(30) Foreign Application Priority Data

Sep. 8, 2016  (KR) .................. 10-2016-0115851

(51) Int. Cl.
| | | |
|---|---|---|
| C07C 29/149 | (2006.01) | |
| B01J 23/62 | (2006.01) | |
| C07C 29/94 | (2006.01) | |
| C07C 35/14 | (2006.01) | |
| C07C 29/17 | (2006.01) | |
| B01J 23/46 | (2006.01) | |
| B01J 35/10 | (2006.01) | |
| B01J 21/08 | (2006.01) | |
| C07C 33/26 | (2006.01) | |

(52) U.S. Cl.
CPC ............ *C07C 29/149* (2013.01); *B01J 23/46* (2013.01); *B01J 23/62* (2013.01); *B01J 23/626* (2013.01); *B01J 35/1019* (2013.01); *B01J 35/1057* (2013.01); *B01J 35/1066* (2013.01); *C07C 29/17* (2013.01); *C07C 29/94* (2013.01); *C07C 35/14* (2013.01); *B01J 21/08* (2013.01); *B01J 2523/43* (2013.01); *B01J 2523/821* (2013.01); *B01J 2523/828* (2013.01); *C07C 33/26* (2013.01)

(58) Field of Classification Search
CPC ... C07C 29/149; C07C 51/36; C07C 31/1355; C07C 61/08; C07C 61/09; C07C 13/276; C07C 2601/14; C07C 33/26; B01J 23/46; B01J 35/1066; B01J 35/1057; B01J 35/1019; B01J 23/626; B01J 21/08; B01J 2523/828; B01J 2523/821
See application file for complete search history.

(56) References Cited

U.S. PATENT DOCUMENTS

| | | | |
|---|---|---|---|
| 3,334,149 A | 8/1967 | Akin et al. | |
| 6,187,968 B1 | 2/2001 | Itoh et al. | |
| 6,294,703 B1 | 9/2001 | Hara et al. | |
| 8,877,984 B2 | 11/2014 | Barton et al. | |
| 2015/0183699 A1* | 7/2015 | Hembre ............... | C07C 29/149 252/182.12 |

FOREIGN PATENT DOCUMENTS

| | | |
|---|---|---|
| JP | 3-184928 A | 8/1991 |
| JP | H6-321823 A | 11/1994 |
| JP | 3108736 B2 | 11/2000 |
| JP | 2001-300327 A | 10/2001 |
| JP | 4595158 B2 | 12/2010 |
| KR | 1999-0064411 A | 8/1999 |
| KR | 10-2008-0098758 A | 11/2008 |
| KR | 10-2016-0056211 A | 5/2016 |
| KR | 10-1619399 B1 | 5/2016 |
| WO | WO 2015/156582 A1 | 10/2015 |

OTHER PUBLICATIONS

JP 4595158, Mitsubishi Gas Chemical Co, Machine Translation, Oct. 30, 2001.*
JP 2015054828, Mitsubishi Gas Chemical Co, Machine Translation, Mar. 23, 2015.*
International Search Report and the Written Opinion of the International Searching Authority for corresponding PCT/KR2017/009715, dated Nov. 29, 2017, 11 pages.

* cited by examiner

*Primary Examiner* — Jafar F Parsa
(74) *Attorney, Agent, or Firm* — Lewis Roca Rothgerber Christie LLP

(57) ABSTRACT

The present invention relates to a method for preparing high-purity 1,3-cyclohexanedimethanol capable of achieving a high conversion rate by allowing most of the reactant to participate in the reaction, and of increasing reaction efficiency and economic efficiency by further simplifying the reaction process, while minimizing by-products within a shorter period of time.

Specifically, the method for preparing 1,3-cyclohexanedimethanol includes reducing 1,3-cyclohexanedicarboxylic acid in the presence of a metal catalyst, which is fixed to a silica support and includes a ruthenium (Ru) compound, a tin (Sn) compound and a platinum (Pt) compound in a weight ratio of 1:0.8 to 1.2:1.2 to 2.4.

13 Claims, No Drawings

METHOD FOR PREPARING 1,3-CYCLOHEXANEDIMETHANOL

CROSS-REFERENCE TO RELATED APPLICATIONS

This application is a National Phase Patent Application and claims priority to and the benefit of International Application Number PCT/KR2017/009715, filed on Sep. 5, 2017, which claims priority to and the benefit of Korean Patent Application No. 10-2016-0115851, filed on Sep. 8, 2016, in the Korean Intellectual Property Office, the disclosure of each of which is incorporated herein in its entirety by reference.

TECHNICAL FIELD

The present invention relates to a method for preparing 1,3-cyclohexanedimethanol. More specifically, the present invention relates to a method for preparing high-purity 1,3-cyclohexanedimethanol capable of achieving a high conversion rate by allowing most of a reactant to participate in a reaction, and of increasing reaction efficiency and economic efficiency by further simplifying the reaction process, while minimizing by-products within a shorter period of time.

BACKGROUND ART

A conventional method for preparing 1,3-cyclohexanedimethanol is a method of forming dimethyl isophthalate through an esterification reaction of isophthalic acid, and then carrying out a hydrogenation reaction using the same to synthesize 1,3-cyclohexanedimethanol via 1,3-dimethyl cyclohexane dicarboxylate at a considerably high temperature and high pressure. However, these techniques have disadvantages in that they involve complex process steps and require a high pressure and thus are uneconomical.

Japanese Unexamined Patent Publication No. 1991-184928 discloses a method for producing 1,3-cyclohexanedimethanol by subjecting 1,3-cyclohexanedicarboxylate diethylhexyl to a hydrogenation reaction in the presence of an alkali metal co-catalyst, such as barium, using a copper chromite catalyst. However, this preparation method utilizes 1,3-cyclohexanedicarboxylate diethylhexyl as a raw material, and thus due to the special nature of raw materials, it is difficult to obtain raw materials, and a down-flow method is employed as a reaction method, which is industrially disadvantageous.

U.S. Pat. No. 8,877,984 discloses a process for the preparation of 1,3-cyclohexane-dimethanol by esterification of isophthalic acid and subsequent hydrogenation. However, there are disadvantages in that the hydrogenation reaction should be carried out sequentially in two steps from the esterified material, and thus the process is complicated and a considerably high pressure and much time are required.

Therefore, there is a need to develop a new preparation process technique capable of replacing the process for preparing 1,3-cyclohexanedimethanol conventionally known in the art.

PRIOR ART DOCUMENTS

Patent Documents (Patent Document 1) Japanese Unexamined Patent Publication No. 1991-184928
(Patent Document 2) U.S. Pat. No. 8,877,984

DETAILED DESCRIPTION OF THE INVENTION

Technical Problem

An object of the present invention is intended to provide a method for preparing 1,3-cyclohexanedimethanol including: reducing 1,3-cyclohexanedicarboxylic acid in the presence of a metal catalyst fixed to a silica support and containing a ruthenium (Ru) compound, a tin (Sn) compound and a platinum (Pt) compound in a weight ratio of 1:0.8 to 1.2:1.2 to 2.4.

Hereinafter, the method for preparing 1,3-cyclohexanedimethanol according to specific embodiments of the present invention will be described in more detail.

Technical Solution

According to one embodiment of the present invention, a method for preparing 1,3-cyclohexanedimethanol including: reducing 1,3-cyclohexanedicarboxylic acid in the presence of a metal catalyst fixed to a silica support and containing a ruthenium (Ru) compound, a tin (Sn) compound and a platinum (Pt) compound in a weight ratio of 1:0.8 to 1.2:1.2 to 2.4, may be provided.

The present inventors conducted studies on a method for synthesizing cycloalkane diol by direct hydrogenation of an alicyclic dicarboxylic acid, and found through experiments that when a metal catalyst fixed to a specific support and satisfying a weight ratio between specific active components is used, high purity 1,3-cyclohexanedimethanol can be prepared with a high conversion rate at a relatively mild temperature and pressure condition through a simplified process as compared with a conventional process, thereby completing the present invention.

Specifically, when 1,3-cyclohexanedicarboxylic acid is reduced using a metal catalyst fixed to a silica support and containing a ruthenium (Ru) compound, a tin (Sn) compound and a platinum (Pt) compound in a specific weight ratio, almost all of the 1,3-cyclohexanedicarboxylic acid, which is a reactant, can participate in the reaction to achieve a high conversion rate, and thus it is possible to provide 1,3-cyclohexanedimethanol having high purity while minimizing by-products within a shorter period of time.

In addition, in the preparation method of one embodiment, the metal catalyst is used in a state in which the active components thereof are fixed to a specific silica support. As the active components are fixed to the silica support, it is possible to achieve the result that a high reaction conversion rate of 90% or more is secured and also the selectivity of 1,3-cyclohexanedimethanol in the finally prepared product is ensured at 89% or more. These effects are considered to be attributed to the influence of a smooth reaction according to the pore characteristics of the silica support.

Further, according to the method for preparing 1,3-cyclohexanedimethanol according to one embodiment, the generation of by-products is minimal during the synthesis of 1,3-cyclohexanedimethanol from 1,3-cyclohexanedicarboxylic acid, so that additional process or step for separating and recovering the by-products may be omitted, and a purification process for increasing purity may be minimized. Furthermore, the method for preparing 1,3-cyclohexanedimethanol according to one embodiment allows a design of a relatively simplified reaction process and may provide high purity 1,3-cyclohexanedimethanol in a high yield within a shorter period of time, thereby improving the efficiency and economy of the entire preparation process.

Specifically, the method for preparing 1,3-cyclohexanedimethanol according to one embodiment may include reducing 1,3-cyclohexanedicarboxylic acid in the presence of a metal catalyst fixed to a silica support and containing a ruthenium (Ru) compound, a tin (Sn) compound and a platinum (Pt) compound in a weight ratio of 1:0.8 to 1.2:1.2 to 2.4

As the metal catalyst, a ruthenium (Ru) compound, a tin (Sn) compound, and a platinum (Pt) compound may be used as active components, and the active components may be fixed to a silica support. A method for preparing the metal catalyst described above is not particularly limited, and may be carried out by a supporting method commonly used when supporting a catalytically-active metal on a porous support in the technical field to which the present invention belongs.

Specifically, the silica support included in the metal catalyst may have a specific surface area of 100 to 500 $m^2/g$, 200 to 300 $m^2/g$, or 250 to 260 $m^2/g$. When the specific surface area of the silica support is too small, the active sites of the reactant and the catalyst are reduced, so that the reaction may not smoothly proceed, or the metal, which plays an important role in the catalyst, may not be properly supported on the support, and thus a phenomenon in which pores are clogged or broken may occur. Further, when the specific surface area of the silica support is too large, a degree of dispersion of the catalyst metal may be excessively increased, and thus the reaction may not rather proceed smoothly.

The total pore volume of the silica support included in the metal catalyst may be 2 $cm^3/g$ or less, 0.5 to 2 $cm^3/g$, 1 to 2 $cm^3/g$, 1 to 1.5 $cm^3/g$, or 1 to 1.1 $cm^3/g$. Examples of the method for measuring a pore volume are not particularly limited, and, for example, a BET measurement method may be used. When the total pore volume of the silica support contained in metal catalyst is too large, the reaction rate between the reactant and the catalyst may be excessively accelerated, so that by-products may be generated in an excessive amount. Also, the metal, which is the active component, may not be sufficiently dispersed, so that remaining reaction byproducts may be generated in an excessive amount or dispersion of the metal as the active component is not sufficiently performed. Consequently, the contact efficiency of the reactant and the catalyst may greatly decrease, and thus the reaction may not rather proceed smoothly.

The average pore diameter of the silica support contained in the metal catalyst may be 80 to 200 Å, or 100 to 120 Å. The average pore diameter refers to an average value of diameter with respect to the pores having various diameters contained in the silica support.

The silica support may include at least one compound selected from the group consisting of silica, silica-alumina, and silica-magnesia.

In addition, the water content of the silica support included in the metal catalyst may be 0.1 to 10% by weight. The 'water content' of a support is defined as a percentage of the weight of water contained in the support with respect to the total weight of the support.

The silica support before supporting the catalyst may can naturally absorb moisture at the humidity of average climatic conditions to contain moisture in an amount of 10% by weight or less. When the water content of the silica support is too high, the volume of the supporting solution for dissolving metal components may be reduced, and when the catalyst is prepared at an excessively high concentration, the degree of dispersion may decrease, and also, the silica support may be used with a reduced water content as needed through a separate drying process. However, applying a separate drying step may be omitted or added from an economic point of view with respect to the cost of catalyst preparation.

The silica support contained in the metal catalyst may be prepared by various methods and may take various structures and shapes. For example, it may be in the form of processed pellets of several millimeters in size, which may be processed by extrusion from particles having an outer diameter of a nano or micro size, and the shape and size thereof are not limited.

In this way, as the silica support is used as a support for supporting the active components in the metal catalyst, it is possible to have a technical advantage that a catalyst having improved selectivity and durability as compared with zeolite or activated carbon, which has been conventionally used, may be prepared. In the case of a zeolite support, there is a disadvantage in that an aluminum component structurally contained therein may be eluted to cause the disintegration of a micropore structure, and the eluted aluminum component may cause a side reaction in the reaction system or may act as an unnecessary substance in a separation and purification step. In the case of an activated carbon support, there are disadvantages in that a high-temperature heat treatment process cannot be applied due to its characteristics, and that the binding between the support and the metal active component is relatively weak, thereby increasing the likelihood of the active components being separated and lost.

Meanwhile, the ruthenium contained in the metal catalyst appears to play a role in converting dicarboxylic acid to primary alcohol, the tin appears to play a role in increasing the selectivity of the alcohol as a synthesis product, and the platinum seems to play a role in suppressing a side reaction by increasing activity of the catalyst.

When the 1,3-cyclohexanedicarboxylic acid is reduced in the presence of the metal catalyst, a reaction product including 1,3-cyclohexanedimethanol may be formed.

The metal catalyst may include a ruthenium (Ru) compound, a tin (Sn) compound and a platinum (Pt) compound in a weight ratio of 1:0.8 to 1.2:1.2 to 2.4, 1:1:0.9 to 1.1:1.6 to 2.0, or 1:0.95 to 1.05:1.7 to 1.9. More specifically, the metal catalyst may include the ruthenium (Ru) contained in the ruthenium (Ru) compound, the tin (Sn) contained in the tin (Sn) compound, and the platinum (Pt) contained in the platinum compound in a weight ratio of 1:0.8 to 1.2:1.2 to 2.4, 1:0.9 to 1.1:1.6 to 2.0, or 1:0.95 to 1.05:1.7 to 1.9.

As confirmed in the examples to be described later, by using the metal catalyst including the ruthenium (Ru) compound, the tin (Sn) compound, and the platinum (Pt) compound in the specific weight ratio, a high conversion rate may be achieved by allowing almost all of 1,3-cyclohexanedicarboxylic acid used as a reactant to participate in the reaction, and the selectivity of 1,3-cyclohexanedimethanol in the finally prepared reaction product may be highly maintained.

The ruthenium (Ru) compound refers to a ruthenium metal itself, an organic salt of ruthenium, or an inorganic salt of ruthenium (e.g., halide or halide hydrate). The same applies to the tin (Sn) compound and the platinum (Pt) compound.

The metal catalyst may include the ruthenium (Ru) compound in an amount of 0.5 to 10% by weight or 0.5 to 1.5% by weight. The amounts of the tin (Sn) compound and the platinum (Pt) compound in the metal catalyst may be determined by the amount of the ruthenium compound and a weight ratio between the metal compounds.

When the amounts of the ruthenium (Ru) compound, the tin (Sn) compound, and the platinum (Pt) compound in the metal catalyst are too small, efficiency of the reduction reaction may be reduced, or the selectivity of 1,3-cyclohexanedimethanol in the finally prepared reaction product may be reduced. Also, a reaction yield may be reduced due to the formation of unreacted carboxylic acid or carboxylic anhydride, and the efficiency may be reduced or energy consumption may be increased when the final reaction product is separated or recovered.

Further, when the amounts of the ruthenium (Ru) compound, the tin (Sn) compound, and the platinum (Pt) compound in the metal catalyst are too large, additional reactions may take place in excess, and thus a primary alcohol type, hydrolysis thereof, or an alkane equivalent thereto may be formed to reduce the reaction yield or reduce the purity of the final reaction product. In addition, a multi-step process must be further carried out in order to remove the generated by-products, and thus, economic efficiency of the process may also be reduced.

In particular, the metal catalyst may include the platinum (Pt) compound, as an active component, in an excess amount as compared with a conventional metal catalyst, so as to achieve a high conversion rate and selectivity in the reduction process of 1,3-cyclohexanedicarboxylic acid used as a reactant. Thus, a further improved conversion rate and selectivity may be achieved compared to when a conventional metal catalyst containing a small amount of platinum (Pt) relative to the amount of ruthenium (Ru) or tin (Sn) is used.

In particular, the metal catalyst may include the tin (Sn) compound in an amount of 30 to 80 parts by weight, or 40 to 70 parts by weight relative to 100 parts by weight of the platinum (Pt) compound. When the tin (Sn) compound is contained in an excessively small amount of less than 30 parts by weight relative to 100 parts by weight of the platinum (Pt) compound, the effect of improving the selectivity of the alcohol due to the tin compound may not be sufficiently achieved. When the tin (Sn) compound is contained in an excessively large amount of more than 80 parts by weight relative to 100 parts by weight of the platinum (Pt) compound, the effect of improving the catalytic activity due to the platinum may not be sufficiently achieved, so that the conversion rate of 1,3-cyclohexanedicarboxylic acid as a reactant may be remarkably reduced to about 20% to 30%, and thus, the selectivity of 1,3-cyclohexanedimethanol in the product may also be reduced to about 20% to 30%.

In addition, the metal catalyst may include the ruthenium (Ru) compound in an amount of 30 to 80 parts by weight, or 40 to 70 parts by weight relative to 100 parts by weight of the platinum (Pt) compound.

Meanwhile, in the step of reducing 1,3-cyclohexanedicarboxylic acid, various reduction methods may be used, and, for example, the reduction method may include contacting the 1,3-cyclohexanedicarboxylic acid with hydrogen gas.

In the step of reducing 1,3-cyclohexanedicarboxylic acid, a method, reaction conditions, and an apparatus known to be used in a reduction reaction of alicyclic carboxylic acid may be used without particular limitation, and, for example, the step of reducing 1,3-cyclohexanedicarboxylic acid may be carried out at a temperature of 50 to 350° C., or 100 to 300° C. under a pressure of 30 to 150 bar, or 40 to 120 bar.

Specifically, the step of reducing 1,3-cyclohexanedicarboxylic acid may be carried out by introducing hydrogen gas and increasing an internal temperature, after converting the inside of a reactor in which the metal catalyst and the 1,3-cyclohexanedicarboxylic acid are present to an atmosphere of inert gas.

That is, the step of reducing 1,3-cyclohexanedicarboxylic acid may include mixing the metal catalyst and the 1,3-cyclohexanedicarboxylic acid in the inside of a reactor under an atmosphere of inert gas; introducing hydrogen gas into the reactor; and raising the temperature of the reactor to carry out a reduction reaction.

The inert gas means including not only the gas components of Group 18 in the periodic table, but also other gases which do not directly affect the hydrogenation reaction, such as nitrogen gas.

In the step of reducing 1,3-cyclohexanedicarboxylic acid, the metal catalyst may be used in an amount of 10 to 300 parts by weight, 50 to 300 parts by weight, or 50 to 200 parts by weight relative to 100 parts by weight of the 1,3-cyclohexanedicarboxylic acid, in the reaction system in which 1,3-cyclohexanedicarboxylic acid as a reactant, the metal catalyst, and a reaction solvent are mixed.

When the content or the used amount of the metal catalyst relative to the 1,3-cyclohexanedicarboxylic acid is too low, the efficiency of the reduction reaction may be reduced, or the selectivity of the 1,3-cyclohexanedimethanol in the finally prepared reaction product may be reduced. When the content of the catalyst is less than the above range, the production efficiency of the reaction apparatus may be reduced, and when the final product is obtained and then separated/recovered, the degradation in efficiency of the apparatus or the energy consumption may be excessive.

Also, when the content or the used amount of the metal catalyst relative to the 1,3-cyclohexanedicarboxylic acid is too high, by-products are generated in an excessive amount during the progress of the reaction, and thus, in order to remove the by-products, a multi-step process must be additionally carried out, which is uneconomical, and the purity of the finally prepared product may be reduced.

Meanwhile, in the method for preparing 1,3-cyclohexanedimethanol, by carrying out a direct reduction reaction using 3-cyclohexanedicarboxylic acid as a reactant, the process may be quickly completed in a single step, and since two or more multi-step processes are not carried out, the process efficiency such as productivity and economic efficiency may be improved.

In step of reducing 1,3-cyclohexanedicarboxylic acid, the reactant itself can also undergo a direct reduction reaction, and a reduction reaction may occur in a state in which the reactant is present in a solvent phase.

Examples of the usable solvent are not particularly limited, and, for example, water or an organic solvent may be used. As an example of the organic solvent, aliphatic alcohols, such as methanol, ethanol, propanol, and cyclohexanol, aliphatic hydrocarbons, such as hexane and cyclohexane, ethers, such as diethyl ether and tetrahydrofuran, or a mixture of two or more thereof may be used.

The amount of the organic solvent used is not particularly limited, and, for example, the organic solvent may be used in an amount of 10% to 1,000% relative to the weight of 1,3-cyclohexanedicarboxylic acid which is a reactant.

The method for preparing 1,3-cyclohexanedimethanol of one embodiment may further include separating the catalyst and then purifying the reaction product at the time of the completion of the reduction reaction process. A method that can be used for the purification is not particularly limited, but the separation and purification may be carried out by distillation, extraction, or chromatography methods.

Meanwhile, the method for preparing 1,3-cyclohexanedimethanol according to one embodiment may have a conversion rate defined by the following Equation of 90% or more, 95% or more, 99% or more, 90% to 100%, 95% to 100%, or 99% to 100%.

Conversion rate (%)=[(Amount of 1,3-cyclohexanedicarboxylic acid added (mol %))−(Amount of 1,3-cyclohexanedicarboxylic acid remaining after reaction (mol %))]/[Amount of 1,3-cyclohexanedicarboxylic acid added (mol %)]*100. [Equation]

As the conversion rate according to the above Equation increases, it can be implied that the reaction was proceeded by 1,3-cyclohexanedicarboxylic acid added as a reactant, and it can also be confirmed that as the method for preparing 1,3-cyclohexanedimethanol according to one embodiment satisfies the high conversion rate, it exhibits high reactivity due to the metal catalyst.

Advantageous Effects

According to the present invention, a method for preparing high purity 1,3-cyclohexanedimethanol capable of achieving a high conversion rate by allowing most of the reactant to participate in the reaction, and of increasing reaction efficiency and economic efficiency by further simplifying the reaction process, while minimizing by-products in a shorter period of time, may be provided.

DETAILED DESCRIPTION OF THE EMBODIMENTS

The present invention will be described in more detail by way of Examples shown below. However, these Examples are given for illustrative purposes only, and the scope of the invention is not intended to be limited to or by these Examples.

Preparation Examples: Preparation of Metal Catalyst

Preparation Example 1

Tin chloride dihydrate, ruthenium chloride trihydrate and chloroplatinic acid hexahydrate were weighed and dissolved in an aqueous solution of hydrogen chloride at 0.1 normal concentration to prepare a metal precursor solution. The metal precursor solution was dripped by the internal pore volume of a silica support [specific surface area: about 255 $m^2/g$, total pore volume: 1.03 $cm^3/g$, average pore diameter: 110 Å] to support the catalyst, followed by drying the catalyst at 120° C. for 12 hours. Thereafter, the catalyst was calcined at 600° C. under an air condition to obtain a catalyst in which ruthenium, tin, and platinum were supported in the form of a composite metal (weight ratio of ruthenium (Ru), tin (Sn) and platinum (Pt) is as shown in Table 1 below).

Preparation Example 2

A metal catalyst was prepared in the same manner as in Preparation Example 1, except that the weight ratio of ruthenium (Ru), tin (Sn), and platinum (Pt) was changed as shown in Table 1 below.

Preparation Example 3

A metal catalyst was prepared in the same manner as in Preparation Example 1, except that the weight ratio of ruthenium (Ru), tin (Sn), and platinum (Pt) was changed as shown in Table 1 below.

Preparation Example 4

A metal catalyst was prepared in the same manner as in Preparation Example 1, except that a Y-zeolite was used instead of a silica support.

Examples 1 and 2: Preparation of 1,3-Cyclohexanedimethanol

Example 1

The metal-supported catalyst obtained in Preparation Example 1, 1,3-cyclohexanedicarboxylic acid, and ion-exchange water were charged into a 500 ml high-pressure reactor equipped with a stirrer so as to satisfy the weight ratios shown in Table 1 below. After replacing the atmosphere in the high-pressure reactor with nitrogen at room temperature, the temperature inside the high-pressure reactor was raised to 230° C. while introducing hydrogen gas into the high-pressure reactor, thereby carrying out hydrogenation reaction under a pressure of 100 bar. At this time, the stirring speed in the high-pressure reactor was fixed to 350 rpm and the reaction was carried out for 3 hours. When the reaction time was reached, the inside of the reactor was cooled to room temperature and the reactor was dismantled to collect a reaction product. Water was removed from the collected reaction product by distillation using a rotary evaporator to obtain 1,3-cyclohexanedimethanol as a final product.

Example 2

1,3-cyclohexanedimethanol was prepared in the same manner as in Example 1, except that 20 wt % of 1,3-CHDA was charged and the reaction was carried out for 3.5 hours, as shown in Table 1 below.

Comparative Examples 1 to 3: Preparation of 1,3-Cyclohexanedimethanol

Comparative Example 1

1,3-cyclohexanedimethanol was prepared in the same manner as in Example 1, except that the metal-supported catalyst obtained in Preparation Example 2 was charged.

Comparative Example 2

1,3-cyclohexanedimethanol was prepared in the same manner as in Example 1, except that the metal-supported catalyst obtained in Preparation Example 3 was used.

Comparative Example 3

1,3-cyclohexanedimethanol was prepared in the same manner as in Example 1, except that the metal-supported catalyst obtained in Preparation Example 4 was used.

Experimental Example: Measurement of Physical Properties of 1,3-Cyclohexanedimethanol Obtained in Examples and Comparative Examples The physical properties of 1,3-cyclohexanedimethanol obtained in the above Examples and Comparative Examples were measured by the following methods, and the results are shown in Table 1 below.

Experimental Example 1: Conversion Rate and Selectivity

The conversion rate of the reactant (1,3-cyclohexanedicarboxylic acid) and the selectivity of 1,3-cyclohexanedimethanol were measured for the final products obtained in the Examples and Comparative Examples using gas chromatography (GC).

Specifically, the reaction product obtained by the reduction reaction (hydrogenation) of the reactant (1,3-cyclohexanedicarboxylic acid) was diluted with methanol. The diluted solution was analyzed by gas chromatography (GC) to determine the selectivity and conversion rate according to the following Equation. In Equation, each numerical value was converted to a unit of molar ratio (%) and applied.

Selectivity (%)=[(Amount of 1,3-cyclohexanedimethanol (mol %)/Amount of reaction product (mol %))*100]

Conversion rate (%)=[(Amount of 1,3-cyclohexanedicarboxylic acid added (mol %))−(Amount of 1,3-cyclohexanedicarboxylic acid remaining after reaction (mol %))]/[Amount of 1,3-cyclohexanedicarboxylic acid added (mol %)]*100.

<Gas Chromatography (GC) Conditions>
1) Column: Agilent 19091J-413 (column length: 30 m, internal diameter: 0.32 mm, film thickness: 0.25 µm)
2) GC system: Gas Chromatography Model Agilent 7890
3) Carrier Gas: Helium
4) Detector: Flame Ionization Detector (FID)

TABLE 1

Results of Experimental Example 1 of Examples and Comparative Examples

| Category | Reactants (wt % in reaction system) 1,3-CHDA | Catalyst Ru/Sn/Pt (wt % in supported catalyst) | Support | (wt % in reaction system) | Time h | Conversion rate (%) 1,3-CHDA | Selectivity (%) 1,3-CHDM | HMCA | Others |
|---|---|---|---|---|---|---|---|---|---|
| Example 1 | 10 | 1/1/1.8 | Silica | 20 | 3 | 100 | 97.7 | 2.3 | 0 |
| Example 2 | 20 | 1/1/1.8 | Silica | 20 | 3.5 | 100 | 89.5 | 2.5 | 8.0 |
| Comparative Example 1 | 10 | 1/1/0.6 | Silica | 20 | 3 | 28.8 | 21.5 | 64.2 | 14.3 |
| Comparative Example 2 | 10 | 1/1/0 | Silica | 20 | 3 | 14.3 | 0 | 69.9 | 30.1 |
| Comparative Example 3 | 10 | 1/1/1.8 | Y-zeolite | 20 | 3 | 100 | 60.3 | 1.2 | 38.5 |

As shown in Table 1, it was confirmed that in Example 1, the 1,3-cyclohexanedicarboxylic acid as the reactant was converted at 100%, and the selectivity of the 1,3-cyclohexanedimethanol in the generated product was 90% or more. In the case of Example 2, it can be seen that even when the amount of 1,3-cyclohexanedicarboxylic acid to be reacted was increased, it showed the conversion rate of 100%, and the selectivity of the generated 1,3-cyclohexanedimethanol was 89% or more which was excellent.

In contrast, when the catalyst in which the amount of the supported-platinum metal was reduced, while maintaining the amounts of the reactant and the catalyst added was used, it showed a reduction in the conversion rate as shown in Comparative Example 1, and the selectivity of the finally prepared product was remarkably reduced. It could be confirmed that even in the case of Comparative Example 2 using the catalyst in which the platinum metal was not supported, the conversion rate was decreased by a level of 14% and 1,3-cyclohexanedimethanol was not generated.

In addition, it could be confirmed that in the case of Comparative Example 3 using a zeolite-based compound as a support, the selectivity of 1,3-cyclohexanedimethanol was shown as 60.3% which was very low, and thus, in the Examples using the specific silica support, a high selectivity could be achieved.

The invention claimed is:

1. A method for preparing 1,3-cyclohexanedimethanol, the method comprising:
reducing 1,3-cyclohexanedicarboxylic acid in the presence of a metal catalyst, which is fixed to a silica support and includes a ruthenium (Ru) compound, a tin (Sn) compound and a platinum (Pt) compound in a weight ratio of 1:0.8 to 1.2:1.6 to 2.4.

2. The method for preparing 1,3-cyclohexanedimethanol of claim 1, wherein the silica support included in the metal catalyst has a specific surface area of 100 to 500 m²/g.

3. The method for preparing 1,3-cyclohexanedimethanol of claim 1, wherein a total pore volume of the silica support included in the metal catalyst is 2 cm³/g or less.

4. The method for preparing 1,3-cyclohexanedimethanol of claim 1, wherein an average pore diameter of the silica support contained in the metal catalyst is 80 to 200 Å.

5. The method for preparing 1,3-cyclohexanedimethanol of claim 1, wherein a water content of the silica support contained in the metal catalyst is 0.1 to 10% by weight.

6. The method for preparing 1,3-cyclohexanedimethanol of claim 1, wherein the metal catalyst includes 0.5 to 10% by weight of the ruthenium (Ru) compound.

7. The method for preparing 1,3-cyclohexanedimethanol of claim 1, wherein the metal catalyst includes 30 to 80 parts by weight of the tin (Sn) compound relative to 100 parts by weight of the platinum (Pt) compound.

8. The method for preparing 1,3-cyclohexanedimethanol of claim 1, wherein the step of reducing 1,3-cyclohexanedicarboxylic acid includes contacting the 1,3-cyclohexanedicarboxylic acid with hydrogen gas.

9. The method for preparing 1,3-cyclohexanedimethanol of claim 1, wherein the step of reducing 1,3-cyclohexanedicarboxylic acid is carried out at 50 to 350° C.

10. The method for preparing 1,3-cyclohexanedimethanol of claim 1, wherein the step of reducing 1,3-cyclohexanedicarboxylic acid is carried out under a pressure of 30 to 150 bar.

11. The method for preparing 1,3-cyclohexanedimethanol of claim 1, wherein the metal catalyst is 10 to 300 parts by weight in amount relative to 100 parts by weight of the 1,3-cyclohexanedicarboxylic acid.

12. The method for preparing 1,3-cyclohexanedimethanol of claim 1, wherein the metal catalyst includes the ruthenium (Ru) compound, the tin (Sn) compound and the platinum (Pt) compound in a weight ratio of 1:0.9 to 1.1:1.6 to 2.0.

13. The method for preparing 1,3-cyclohexanedimethanol of claim 1, wherein a conversion rate defined by the following Equation is 90% or more:

conversion rate (%)=[(amount of 1,3-cyclohexanedicarboxylic acid added (mol %))−(amount of 1,3-cyclohexanedicarboxylic acid remaining after reaction (mol %))]/[amount of 1,3-cyclohexanedicarboxylic acid added (mol %)]*100. [Equation]

\* \* \* \* \*